United States Patent [19]

Myles et al.

[11] Patent Number: 4,480,041

[45] Date of Patent: Oct. 30, 1984

[54] USE OF PHOSPHOTRIESTER INTERMEDIATES FOR PREPARATION OF FUNCTIONALIZED LIPOSOMES

[75] Inventors: Arthur Myles, Stow; Say-Jong Law, Dedham; Frank X. Cole, Stow, all of Mass.

[73] Assignee: Collaborative Research, Inc., Lexington, Mass.

[21] Appl. No.: 396,678

[22] Filed: Jul. 9, 1982

[51] Int. Cl.³ .................... G01N 33/54; G01N 33/78
[52] U.S. Cl. ............................ 436/508; 435/7; 436/500; 436/528; 436/536; 436/816; 436/817; 436/829
[58] Field of Search ............... 436/829, 528, 536, 816, 436/817, 508, 819

[56] References Cited

U.S. PATENT DOCUMENTS

| | | | |
|---|---|---|---|
| 3,850,578 | 11/1974 | McConnell | 436/829 X |
| 4,255,411 | 3/1981 | Lim | 436/829 X |
| 4,342,826 | 8/1982 | Cole | 436/829 X |
| 4,372,745 | 2/1983 | Mandle | 436/537 |

*Primary Examiner*—Sidney Marantz
*Attorney, Agent, or Firm*—Wolf, Greenfield & Sacks

[57] ABSTRACT

A method of forming an analyte-functionalized liposome for use in immunoassay techniques employs a phosphotriester intermediate of a phospholipid derivatized with the desired analyte in a process of forming a liposome which is functionalized on its outer surface with the analyte and which carries an enzyme marker. The method is also used to functionalize the liposome with a ligand which acts as a leash between the analyte and the liposome. Liposomes produced by the method include penicillin-G-functionalized liposome.

11 Claims, No Drawings

USE OF PHOSPHOTRIESTER INTERMEDIATES FOR PREPARATION OF FUNCTIONALIZED LIPOSOMES

BACKGROUND OF THE INVENTION

Liposomes which can carry enzymes and be labeled with antigens or antibodies are described in British Patent Application No. 8,103,282 dated Feb. 3, 1981. Liposomes labeled with antigens at their external surface and containing an enzyme entrapped in their internal volume are mixed with cognate antibody, complement, enzyme substrate and a test sample to determine whether or not the liposomes permit substrate access to the entrapped enzyme. This determination is made by detecting enzymatic activity in the presence of substrate after exposure to the test sample. Such techniques are referred to as enzyme membrane immunoassay techniques or liposome immunoassays.

A key component of the liposome immunoassay (LIA) is analyte functionalized liposome, (i.e., liposome with covalently attached antigen, antibody, or other substance of interest). Analytes can be introduced into the liposomes during their formation by incorporation of specific quantities of analyte derivatives of phosphatidylethanolamine (PEA) or other phospholipids.

Previous methods of preparation of analyte-functionalized liposomes utilize PEA-diester intermediates for direct coupling with the analyte or its derivatives. Complicated products are generated and difficulties are usually encountered in purifying and characterizing the target compound.

A method of preparing phospholipid-analyte derivatives utilizing a phosphotriester intermediate would avoid some of the difficulties encountered by the diester method. However, no triester method of forming such compounds has previously been shown in the art.

Phosphotriester intermediates, protected with benzyl groups, have been previously described, c.f., J. D. Billimoria and K. O. Lewis; J. Chem. Soc., (C), 1404 (1968). Such described intermediates are used in the preparation of phospholipids but are not applicable to preparation of phospholipid-analyte derivatives, since deprotection of such benzyl ester intermediates to the target analyte derivatized phospholipid is not compatible with most analytes required for the technology of the liposome immunoassay described above. Removal of the benzyl groups by anionic fission with sodium iodide produces benzyl iodide. That by-product is not only difficult to remove but is also a highly reactive alkylating reagent capable of reacting with any nucleophilic group on the analyte.

Use of phosphotriester methodology for different applications in phospholipid chemistry has been previously disclosed by J. H. van Boom. [C. A. A. van Boeckel et. al., Tetrahedron, 37, 3751 (1981); J. J. Oltvoort et. al., Recueil Trav. Chim. Pays-Bas, 101, 87 (1982); C. A. A. van Boeckel and J. H. van Boom, Tetrahedron Letters No. 37, 3561 (1979); C. A. A. van Boeckel and J. H. van Boom, Tetrahedron Letters, 21, 3705 (1980).] These methods disclose use of phosphotriester methodology for synthesis of naturally occurring teichoic acid fragments and modified glycophospholipids for elucidation of their function in membranes and for reasearch investigation of their physiological properties.

SUMMARY OF THE INVENTION

It is an object of the present invention to provide a method of preparing analyte functionalized liposomes for use in liposome immunoassay methods capable of adaptation for any of a large variety of analytes.

It is also an object of the present invention to provide a method of preparing analyte derivatized phospholipids which affords greater ease of synthesis, separation, and/or characterization of intermediates than is possible in previous methods.

It is another object of the present invention to provide a method of preparing analyte derivatized phospholipids which permits ease of production of multigram quantities required for LIA techniques.

It is a further object of the present invention to provide a method of preparing analyte derivatized phospholipids which employs common intermediates useful for preparation of several different analyte derivatized phospholipid compounds.

Another object of the present invention is to provide a method of preparing ligand-functionalized liposomes for the subsequent attachment of an analyte to the ligand group for use in LIA techniques.

A still further and specific object of the present invention is to provide a penicillin-G- or thyroxine-functionalized liposome for use in LIA detection of penicillin or thyroxine.

The present invention is an advance in the state of the art for preparation of analyte derivatized phospholipids. These compounds are a key component of the liposomes required for competitive inhibition assay by the LIA technology. The method utilizes phosphotriester rather than previously used phosphodiester intermediates for synthesis of these derivatives. The intermediates are uncharged compounds which are often far simpler to prepare, purify and characterize than charged diester intermediates. Common intermediates can be used for preparation of several target compounds.

In the present invention, use of phosphotriester methodology is directed toward multigram preparation of analyte or ligand derivatized amphiphilic compounds, specifically phospholipids. Incorporation of such derivatives containing either analytes or ligands plus analytes into liposomes provides the analyte tagged, enzyme laden liposomes required for use in LIA techniques. The same analyte-tagged liposomes, without an enzyme core, can also be used as immunogens as described by Schuster, et al. (J. Immunol., 122, 900 (1979)) and Dancy, et al. (J. Immunol., 122, 638 (1979)).

Incorporation of ligand derivatives without attached analytes provides ligand functionalized liposomes. These can be modified chemically by using condensing or coupling reagents to attach analytes or macromolecules to provide either antigen or antibody tagged, enzyme laden liposomes as required for LIA. Preparation of the ligand-functionalized liposome using the present method is more fully described below.

According to the present invention, a phospholipid is used, having the general formula

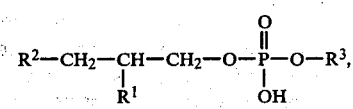

where $R^1$ and $R^2$ can independently be H, OH, R", OR" or

(where R" is a saturated or unsaturated, branched or straight-chain alkyl or alkylene group of 1 to 24 carbons), wherein at least one of $R^1$ or $R^2$ is

or OR"; and where $R^3$ is a side chain with a functional group capable of bonding to the analyte or ligand desired to be attached. The above molecule is amphiphilic, having both a lipophilic portion and a charged portion. The phospholipid is first treated with a protecting group, to form a compound having the structure

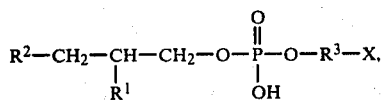

where X is a protecting group for $R^3$. This compound is then treated with an alcohol or activated alkyl halide to afford a phosphotriester having the structure

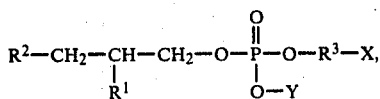

where Y is a phosphotriester blocking group. Once the blocking group is attached, the $R^3$-protecting group is removed and the desired analyte is attached at the $R^3$ site, forming a triester intermediate of the formula

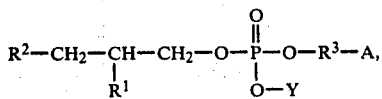

where A is the analyte desired to be attached. The triester and any analyte blocking groups are then removed, leaving an analyte-functionalized phospholipid of the formula

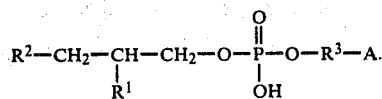

That compound is then used to prepare an enzyme-laden liposome with an external covalently attached analyte functional group.

An alternative to producing a phospholipid with a directly attached analyte is to produce a phospholipid on which the analyte is attached by a ligand which acts as a "leash", or spacer, i.e., the ligand is a bifunctional compound which enables attachment at one end to the desired analyte and the other end to the phospholipid. To produce such a phospholipid compound, the ligand is attached to the phospholipid in the same method as previously described for attaching an analyte. Attachment of a ligand to the phospholipid by the present method would produce the triester intermediate

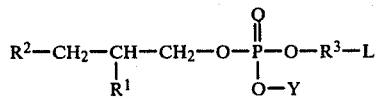

where L is a ligand. One of three approaches may be employed for attachment of an analyte to the ligand to produce the desired functionalized liposome. One approach involves deprotecting the above intermediate and using the phosphodiester ligand intermediate to form a ligand-functionalized liposome, and then attaching the analyte to the ligand functional group. A second approach is to attach the analyte directly to the ligand group of the above intermediate to form a compound having the structure

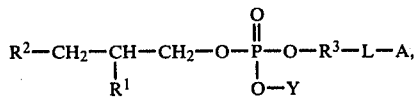

followed by subsequent removal of the triester and any analyte blocking group and use of the phospholipid-ligand-analyte derivative to form the analyte-ligand functionalized liposome.

A third alternative approach to the formation of phospholipid-ligand-analyte combinations is the initial formation of ligand-analyte derivatives, subsequent coupling to the phospholipid, deprotection, and liposome formation. The route chosen for preparation of these ligand derivatives depends very much on the relative stability of the phospholipid and the specific analyte under conditions required for their formation.

This newly developed phosphotriester approach for synthesis of key intermediates provides a rapid and convenient method for the large scale preparation of phospholipid-analyte derivatives. Triester intermediates are quite soluble in organic solvents, can be prepared in high yield, are readily functionalized with various analytes or analyte derivatives, and are easily purified, readily characterized and conveniently converted to the targeted phospholipid-analytes. The methodology has a high degree of flexibility in that triester and analyte blocking groups can be varied to assure compatability with the chemistry of the analyte in question.

The simplicity of the triester methodology is in sharp contrast to the traditional diester synthetic route for preparation of phospholipid-analyte derivatives. Phospholipid diesters are marginally soluble in organic solvents and sometimes react poorly to give a multiplicity of products which can be extremely difficult to purify. In many cases, they are not readily characterized and/or not readily amenable to large scale synthesis as required for commercial production.

As was mentioned earlier herein, van Boom and others have described the use of phosphotriester methodology for synthesis of naturally occurring teichoic acid fragments and modified glycophospholipids. The synthesis of these compounds involves sequential phosphorylation of a glycerol derivative and either a second glycerol derivative or a gentiobiose derivative to form a phosphotriester derivative of the natural product. These protected intermediates are ultimately converted to target compounds by removal of several protecting groups including a phosphotriester group.

The van Boom procedures differ in four ways from those presented herein:

(1) The herein-described phophotriester synthesis starts with an intact preformed naturally occurring phopholipid or a synthetic analog. The procedure described by van Boom uses totally synthetic intermediates.

(2) The herein-described procedures are utilized for synthesis of phospholipid-analyte, or -ligand-analyte derivatives as required for use in immunoassays. These are not naturally occurring compounds. The derivatives described by van Boom are naturally occurring compounds or their derivatives. They are being prepared for elucidation of their function in membranes and for research investigation of their physiological properties.

(3) Different numbers and types of phosphoester linkages are formed during the two reaction procedures. In the presently described procedure, a single phosphoester protecting group is introduced. It functions as a protecting group to convert a charged, chemically reactive phosphodiester into a neutral, chemically inert phosphotriester. This protecting group is removed at a later stage, after conjugation of the phospholipid with the appropriate analyte or ligand and analyte.

The van Boom procedure requires formation of two new phosphoester linkages with two different molecules. These new linkages form a phospholipid backbone which was not present prior to these reactions. These linkages remain intact in the final product. The phosphoester protecting group which is ultimately removed was incorporated as part of the phosphorylating reagent.

(4) One could envision preparation of phospholipid-analyte or -ligand-analyte derivatives by modification of the procedures suggested by van Boom. However, such an approach would be impractical because of the multiplicity of reaction steps involved, low yield in preparation of 1,2-di-o-benzylsn-glycerol, and anticipated low yield in subsequent reactions.

DETAILED DESCRIPTION OF THE PREFERRED EMBODIMENT

In the present invention, synthesis of triester intermediates and conversion to the targeted phospholipid-analyte derivative is a five step process, as outlined schematically in Table 1. A sixth and final step involves incorporation of phospholipid-analyte or ligand-analyte derivatives into analyte tagged, enzyme laden liposomes as required for the LIA assay. An alternative final step involves incorporation of the phospholipid-ligand derivative into the liposome with subsequent coupling to the analyte to form the analyte tagged, enzyme-laden liposome as required for the LIA assay.

In the preferred embodiment of the present method, the phospholipid utilized is a phosphatidylethanolamine (PEA) compound of the formula

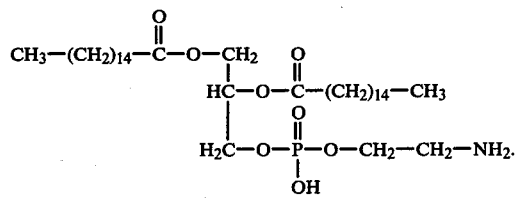

Table 2 shows the reaction sequence of the present method using PEA wherein penicillin-G is the analyte and the final product is penicillin-G-functionalized liposome.

Table 3 summarizes the phosphatidylethanolamine and liposome derivatives prepared to demonstrate utility of the phosphotriester synthetic approach for preparation of analyte-functionalized liposomes.

TABLE I

Preparative Procedures for Synthesis of Analyte Functionalized Liposomes

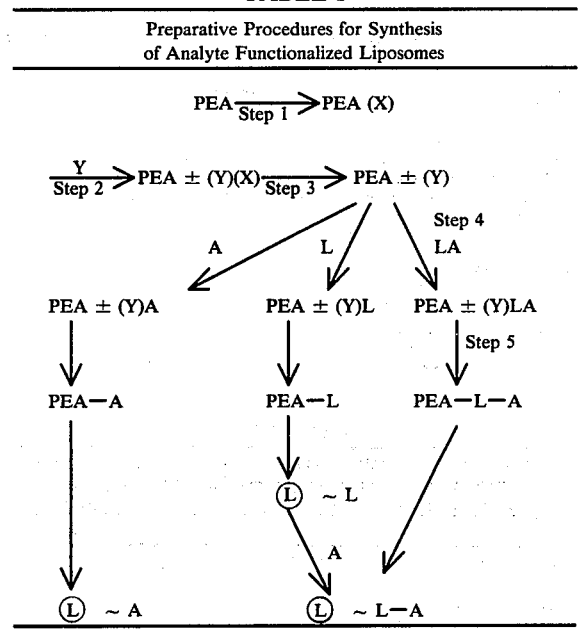

Legend

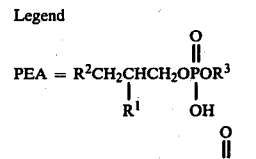

Where $R^1$, $R^2 = CH_3(CH_2)_{14}CO-$
$R^3 = -CH_2CH_2NH_2$
$X = R^3$(amine) protecting group
$\pm Y$ = phosphotriester blocking group
L = ligand
A = analyte
Ⓛ = liposome

TABLE II

Chemical Modifications of Phosphatidylethanolamine for Preparation of Penicillin Functionalized Liposomes

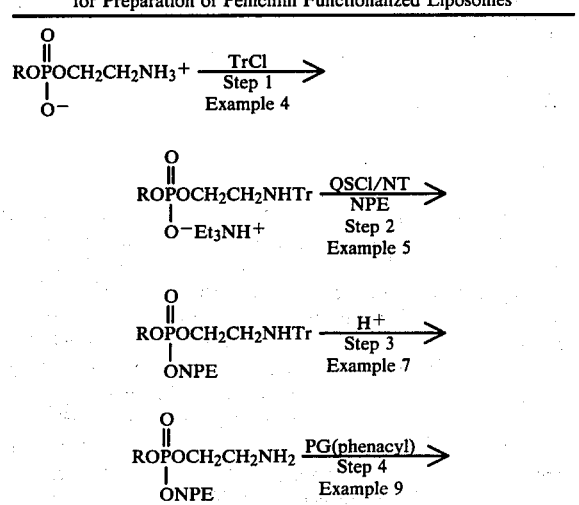

TABLE II-continued
Chemical Modifications of Phosphatidylethanolamine for Preparation of Penicillin Functionalized Liposomes

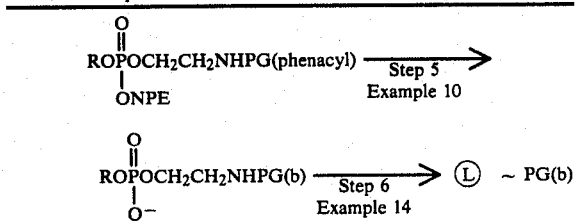

LEGEND
Tr = $(C_6H_5)_3C—$
QSCl = 8-quinolinesulfonylchloride
NT = 3-nitro-1,-2,4-triazole
NPE = 2-(4-nitrophenyl)ethanol
PG(phenacyl) = 2-(4-bromophenyl)-2-oxoethyl benzyl penicillanate
L = liposome

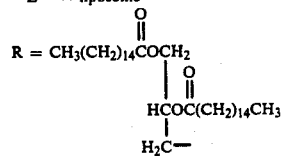

TABLE III
Summary of phosphatidylethanolamine and liposome derivatives prepared to demonstrate utility of the phosphotriester synthetic approach for preparation of analyte functionalized liposomes.

| | X | Y | L | A | Example |
|---|---|---|---|---|---|
| Step 1 | BOC | — | — | — | 1 |
| | Tr | — | — | — | 4 |
| Step 2 | BOC | phenacyl | — | — | 2 |
| | Tr | phenacyl | — | — | 6 |
| | Tr | NPE | — | — | 5 |
| Step 3 | — | phenacyl | — | — | 3 |
| | — | NPE | — | — | 7 |
| Step 4 | — | phenacyl | — | PG(phenacyl) | 8 |
| | — | NPE | — | PG(phenacyl) | 9 |
| | — | phenacyl | suc | — | 11 |
| | — | phenacyl | suc | T4 | 12 |
| | — | phenacyl | suc-ED | PG (phenacyl) | 16 |
| Step 5 | — | — | — | PG | 10 |
| | — | — | suc | T4 | 13 |
| | — | — | suc-ED | PG | 17 |
| Step 6 | — | — | — | PG | 14 |
| | — | — | suc | T4 | 15 |
| | — | — | suc-ED | PG | 18 |

X = amine protecting group
Y = phosphotriester derivative
L = leash
A = analyte
PEA = β,γ-dipalmitoyl-D,L-2-phosphatidylethanolamine
BOC = t-butylcarbonyl
Tr = trityl
phenacyl = 2-(4-bromophenyl)-2-oxoethyl
NPE = 2-(4-nitrophenyl)ethyl
PG(phenacyl) = 2-(4-bromophenyl)-2-oxoethylester of penecillin
suc = succinate
T4 = tetraiodothyronine
3MP = 3-mercaptopropionyl
EAC = ε aminocaproyl
4MB = 4-mercaptobutyryl
ED = ethylenediamine The first step in the synthesis involves selective blocking of the free amine group of the PEA to keep it intact but inert during subsequent reactions. The protecting groups used are standard for protection of primary or secondary amines. The only requirement for their use is the ability to be removed during the third synthetic step without concomitant cleavage of the targeted PEA triester or other key functional groups. Suitable protecting groups include acyl (e.g. trifluoroacetyl, phthaloyl, benzoyl, etc.), alkyl (e.g. triphenylmethyl derivatives, phenacyl, tetrahydropyranyl, etc.), urethanes (e.g. carbobenzoxy [CBZ], t-butoxycarbonyl [t-BOC], fluorenylmethoxycarbonyl [FMOC], etc.) and other (e.g. sulfonyl, silyl, etc.) residues which meet the above criteria.

Examples 1 and 4 below describe the use of t-BOC(t-butylcarbonyl) and trityl (triphenylmethyl) blocking procedures respectively. Tritylation of amine groups of PEA has been previously utilized for amine protection in the synthesis of chemically defined 0-(1,2-diacyl-sn-glycero-3-phosphoryl) ethanolamines. (See R. Aneja et al., Bio Chem. Biophys. Acta; 187, 579 (1969).

The second reaction step involves conversion of the partially protected, but negatively charged, phosphodiester (from step one) to a fully protected neutral phosphotriester or other derivative. The standard route for preparation of these triesters is chemical activation of the phosphodiester and subsequent coupling with an appropriate alcohol. Activating reagents may include but are not limited to carbodiimides (dicyclohexylcarbodiimide [DCC]; 1-ethyl-3[3-dimethylamino-propyl]-carbodiimide [EDC]), sulfonic acid derivatives (2,4,6-triisopropylbenzene sulfonylchloride [TPSCl], mesitylene sulfonyl-3-nitro-1,2,4-triazole [MSNT], 8-quinolinesulfonyl chloride [QSCl]/3-nitro-1,2,4-triazole [NT]) and other ester forming reagents (Lewis or other strong acids, thionyl chloride, acid anhydrides, carbonyl diimidazoles, etc.). Alcohols used for triester synthesis may include but are not limited to 2-(4-nitrophenyl)-ethyl (NPE), trichloroethyl (TCE), tribromoethyl (TBE), cyanoethyl (CE), p-chlorophenyl (PCP), 2,4-dichlorophenyl (DCP) and methyl alcohol. An alternative route for triester formation is reaction of the PEA diester salt with an activated alkyl halide (e.g. methyl iodide, phenacyl bromides, etc.).

Other methods for triester formation include reaction with appropriate diazoalkanes (e.g. diazomethane), orthoesters (e.g. trimethyl orthoformate) or sulfonic acid esters (e.g. dimethyl sulfate).

Example 5 describes conversion of partially protected PEA to the nitrophenethyl ester via an activated phosphodiester intermediate. Examples 2 and 6 describe an alternative esterification procedure using a phenacyl halide.

Step three of the synthetic sequence involves removal of the amine protecting group under conditions which leave the remainder of the PEA triester intact. Conditions required for protecting-group cleavage vary with the type of amine protecting group and the nature of the phosphotriester. Examples 3 and 7 below describe two types of acid cleavage required for removal of BOC and trityl groups, respectively.

Step four of the synthetic sequence involves chemical condensation of an analyte or partially protected analyte derivative with the amine function of the PEA. This is convenient when the analyte has a functional group which can be used to form a covalent linkage with the PEA amine residue. Examples 8 and 9 describe reaction of a protected penicillin derivative with the amine group on two types of triester derivative.

An alternative for step four is introduction of a ligand group which can serve either as a "leash" or as a means of replacing the reactive amine group with a chemically different group. The ligand is normally introduced by initial attachment to the phospholipid and subsequent coupling to the analyte. The latter step can be carried out either prior to or subsequent to incorporation of the phospholipid-ligand into the liposome.

Example 11 describes introduction of the succinate residue as a ligand and a means of changing phospholipid functionality. Example 12 describes coupling of the succinate residue to the analyte thyroxine for preparation of protected PEA±(phenacyl) suc-T4.

"PEA±(phenacyl)-Suc", the product described in Example 11, has been deprotected and incorporated directly into liposomes, giving succinate functionalized liposomes. Prefunctionalization of liposomes with such ligand derivatives of phospholipids, with the same or chemically-altered reactive groups (e.g. amines, carboxylic acids, hydroxides, etc.) provide a means, via crosslinking and coupling reagents (e.g. succinimidyl 3-[2-pyridyldithio]propionate [SPDP], 2-iminothiolane, carbonyl-diimidazole, dicyclohexylcarbodiimide [DCC]), for coupling analytes, and particularly larger molecules, macromolecules (e.g. peptides, proteins, antibodies, enzymes, nucleic acids, etc.) or their derivatives to the liposome surface. Such antigen- or antibody-tagged, enzyme laden liposomes are immunospecifically caused to act on specific enzyme substrates in the presence of cognate antigen or antibody and active complement. Bifunctional crosslinking agents may also be coupled to phospholipids, incorporated into liposomes, and coupled directly to reactive analyte derivatives.

An alternative method for introduction of a ligand between phospholipid and analyte is initial ligand attachment to the analyte with subsequent coupling to the phospholipid component. Examples 16 and 17 describe preparation of a ligand derivative of penicillin-G and its coupling to PEA.

Ligands or spacers are preferably alkyl groups of 20 carbons or less, branched or unbranched, saturated or unsaturated, which contain two distinct functional groups consisting of carboxyl, amine, hydroxyl or sulfhydryl residues, preferably at the opposite ends of the ligand. One end of the ligand is designed for attachment to the phospholipid preferably via a carboxyl group. The other end of the ligand is attached to other ligands or to analytes. The reactive group at this portion of the ligand depends on the chemical nature of the ligand or analyte to which it is being coupled. The actual mechanism for attachment of ligands to phospholipids, analytes or other ligands varies depending on the nature of reaction components. Anhydrides, carbodiimides, sulfonic acid derivatives, N-hydroxysuccinamides, 2-pyridyldithio propionates, thiolanes and other means of activation or reactive group formation are used for introduction of these ligands. In addition to using single-ligand leashes, two or more ligands may be used as spacers between the liposome and the analyte.

Ligands for the previously described reactions may include but are not limited to 6-aminocaproyl, succinoyl, lysyl, diaminoethyl, diaminohexyl, hydroxyethyl, hydrazyl and polylysyl residues. Bifunctional crosslinking agents including but not limited to succinimidyl 3-[2-pyridyldithio]propionate (SPDP) or 2-iminothiolane may also be used to introduce such ligands as 3-mercaptopripionyl or 4-mercaptobutyryl or other groups.

Step five of the synthetic sequence involves removal of the phosphotriester and analyte blocking group under conditions which do not adversely effect the analyte phospholipid linkage or any other function in the molecule. Conditions for this deprotection will vary considerably and depend on the nature of the phospholipid and analyte as well as the triester and analyte protecting groups. Examples 10 and 13 describe preparation of fully deprotected PEA-penicillin-G and "PEA-suc-T4" as required for preparation of analyte functionalized liposomes.

The sixth and final step is the preparation of analyte tagged, enzyme laden liposomes by one of several methods, as will be further discussed below.

Table 2 shows the reaction sequence wherein penicillin-G-functionalized liposomes are produced by the present methods. Details are given in the designated examples.

The term analyte is used herein to refer to those materials which are capable of being coupled to the surface of immunoreactive liposomes, e.g., antigens, antibodies, circulating hormones, antibiotics and other therapeutic drugs, and derivatives thereof, as further described below.

Antigens which can be tested for or used as labels for the liposomes in accordance with this invention are numerous. There are a number of antigens, the quantitation of which is of significance in clinical diagnostics. Many of these are now assayed by radioisotopic methods. Assays for these by the LIA method would be a considerable improvement inasmuch as hazardous, unstable reagents are not employed.

Antigens and antigenic materials which are to be analyzed for LIA purposes include any which by themselves or with other products will produce antibodies cognate therefor and thus detectable by the immune reaction. For example, digoxin is considered an antigen because it with another material will produce antibodies such that the antibody to digoxin can be used in a test with either the antibody or digoxin used as the label depending upon whether one is testing for the digoxin or the cognate antibody. Such materials as bovine serum albumin, key hole limpet heomocyanin or other macromolecular carriers are covalently coupled to the digoxin or other "antigen" in forming antibodies. Thus the word "antigen" as used herein is meant to include all antigenic materials whether antigenic by themselves or in combination with other materials to produce cognate antibodies in animals such as humans, rabbits, goats, sheep, guinea pigs, bovine species and other mammals.

The LIA method may be employed to detect and quantitate specific antibodies directed agains various antigens. The presence as well as the amounts of such antibodies may be taken as indicators of the potential of immunity to various infectious disease, previous exposure to disease, or active infection.

The present method may be utilized to produce analyte-functionalized liposomes to be beneficially applied to the detection and estimation of circulating hormones as indicators of endocrine function by employing LIA techniques. A partial listing of these hormones would include:

| | |
|---|---|
| thyroid hormones | thyroxine and triidothyronine, parathyroid hormone and calcitonin. |
| pancreatic hormones | insulin, proinsulin, and glucagon |
| pituitary hormones | prolactin, adrenocorticotropic hormone, tyrotropin, oxytocin and vasopressin |
| uterine and placental hormones | chorionic gonadetropin, placental lactogens, chorionic thyrotropin and relaxin. |
| steriod hormones | Estradiol, Estrone, Estriol, Testosterone and Dihydrotestosterone. |
| growth factors | Urogastrone, Nerve growth factor |

| -continued |
|---|
| and the somatomedins |

The method may be usefully applied to the intracellular messengers, the cyclic nucleotides and prostaglandins.

The present invention may also be used to prepare analyte-functionalized liposomes to be applied to the LIA screening of circulating levels of therapeutic drugs, e.g. the cardiac glycosides; digoxin, digitoxin, anticonvulsants, diphenylhydantoin, mesantoin, phenobarbital, and mephobarbital. Of particular interest are those drugs with a narrow therapeutic index, i.e., a certain minimal circulating level is required for therapeutic efficacy while a moderately higher level elicits toxic or harmful reactions.

Other analytes applicable to the present method include antibiotics such as penicillin, streptomycin, and tetracyclines, chlortetracycline, oxytetracycline, and tetracycline, chloramphenicol, erythromycin, caromycin, and polymykin B. The aminoglycoside antibiotics gentamycin, amikacin, tobramycin, kanamycin and neomicin employed in the management of aerobic Gram negative bacillary infections can be conveniently assayed by LIA, and corresponding functionalized liposomes may be prepared by the methods of the present invention.

Functionalized liposomes for LIA may also be applied to the detection and estimation of drugs of abuse such as opiates—morphine, heroin, meperidine and methadon; ergot alkaloids, such as lysergic acid diethylamide, marijuana, barbiturates and cocaine and its derivatives. The corresponding phospholipid-analyte derivatives for LIA detection of these substances may be prepared by the present method.

The analytes of the present method may include antigens for LIA diagnosis in environments which are less well-equipped and sophisticated than diagnostic laboratories. For example, the LIA method can be applied to screening food and environmental toxins. In food screening, important antigens would be mycotoxins and natural toxicants. This involves such major toxins as aflatoxins, ochratoxin, patulin, penicillic acid, zearelonone; and tricothecene toxins, as well as toxic metabolites such as ipomeamerone that occur naturally in foods. Beyond the natural toxicants there are a wide variety of environmental contaminants, the presence of which in foods even in trace amounts poses a significant threat to mankind. These may be industrial byproducts or pesticides e.g. polychlorinated biphenyls, chlorinated dibenzo-p-dioxins, chlorinated dibenzofurans, heptachlorepoxide, dieldrin, and DDT 1,1'-2,2,2-Trichloroethylidene)-bis[3-chlorobenzene]; 1,1,1 trichloro-2,2 bis(p-chlorophenyl)ethane.

The analytes of the present method need not be restricted to small molecules as it has been shown (Humphries and McConnell Proc. Nat. Acad. Sci. 71, 1691–1694, 1974) that macromolecular antigens such as egg albumin may be coupled to the surface of immunoreactive liposomes. Thus, the present invention may also be applied to detection of macromolecular antigens-plasma proteins, hepatitis associated antigens, histocompatibility markers.

Small (J. Am. Oil Chem. Soc. 45, 108–117 [1968]) provides a classification of lipids based upon their interaction with water) both in bulk and at the surface. Class II lipids are defined as "insoluble, swelling amphiphilic lipids." Class II lipids include: phosphatidylethanolamines, lecithins, phosphatidyl inositol, sphingomyelin, cerebrosides, phosphatidic acid, plasmalogens, phosphatidyl serine, cardiolipins, and certain plant sulfolipids.

Some Class II lipids are particularly appropriate for the formation of phospholipid-analyte or -ligand-analyte derivatives by the triester technology. These include phosphatidylethanolamine compounds of the formula:

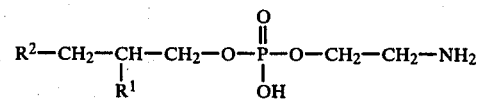

where $R^1$ and $R^2$ can independently be H, OH, R", OR" or

(where R" is a saturated or unsaturated, branched or straight-chain alkyl or alkylene group of 1 to 24 carbons), wherein at least one of $R^1$ or $R^2$ is

or OR".

In these constructions ethanolamine can be substituted by any side chain (P) containing preferably one but also two or more reactive functional groups (Q, R, etc,). P is an inert side chain consisting of 1 to 10 carbon atoms in branched or straight chain form, with saturated or unsaturated linkages and Q, R, etc. are one or more of the combination of amine, carboxyl, hydroxyl, sulfhydryl, ethylene oxide, or any other reactive functional group useful for attachment of analytes or ligands. Particular substitutions for ethanolamine would include N-methyl ethanolamine, serine, and N-2-hydroxyethylalanine.

The liposomes of the present invention are sometimes called smectic mesophases or synthetic vesicles. They are in fact dry lipid films suspended in aqueous media as have been describe by Uemura, K. and Kinsky, S. C. (1972) Biochemistry 11, 4085-4094. Liposomes are belived to consist of lipid bilayers which separate an internal aqueous compartment from an external aqueous media and are in fact prototypes of biological membranes. The liposomes mimic the properties of biological membranes. As is known, they can be made to contain either enzyme substrates or enzymes. For purposes of the present invention, the liposomes contain an enzyme and have an outer surface substantially free of the enzyme which outer surface encloses the enzyme and is labeled with an antigen or its cognate antibody depending upon the test to be carried out. Preferably if one is testing for the antibody, the liposome will be labeled with that antibody while if one is testing for the antigen, the liposome will be labeled with the antigen.

In preparing liposomes, it is necessary that lipids—such as those of Class II—which are insoluble in water be introduced into an aqueous environment. This can be achieved by a variety of methods.

By one such known method, lipids are physically dispersed into an aqueous solution. A dry thin film of lipids is formed on the interior surface of a suitable vessel. The aqueous solution containing the substances to be entrapped within the liposomes is then placed in the vessel in contact with the lipid film. The lipid film is then dispersed into the aqueous solution by vigorous agitation of the vessel (glass beads approximately 0.1 mm in diameter may be included in the vessel to accelerate this dispersion). Also, dispersion of the lipid film may be enhanced by sonication through immersion of the vessel in a bath type sonicator or by immersing the probe of a sonifier into the aqueous solution. Excessive sonication may inactivate enzyme and can produce very small liposomes.

Alternatively, the lipids may be dissolved in an aqueous solution containing a detergent lipid of Class III A or B such as laurylsulfate or sodium deoxycholate. The detergent is then removed (e.g. by dialysis), and the liposome bilayers are formed. Enoch and Strittmatter (Proc. Nat. Acad. Sci. 76, 145–149 (1979)) have described the preparation of 1000 A diameter, single-bilayer liposomes using sodium doxycholate as the detergent which is dialyzed.

Another known technique involves the addition of aqueous solution to a mixture of lipid and a volatile organic solvent which solvent is subsequently removed by evaporation at reduced pressure. Szoka and Papahadjopoulos (Proc. Nat. Acad. Sci. 75, 4194–4198 [1978]) have described preparation of liposomes with very large internal aqueous space by means of evaporation of organic solvents diethyl ether or isopropyl ether.

The physical and detergent dialysis methods are particularly appropriate to the present invention, as these produce acceptably large vesicles and are quite gentle, thus unlikely to inactivate the enzymes. In cases where organic solvent evaporation is to be employed, it is necessary that the enzyme to be encapsulated should be insensitive to that solvent. For example, vesicles of this type can be prepared containing alkaline phosphatase which enzyme is not denatured by the diethyl ether used in the process. Examples 14, 15 and 18 describe application of these methods.

EXAMPLES

EXAMPLE 1

Preparation of
N-tert-Butyloxycarbonyl-$\beta,\gamma$-dipalmitoyl-D,L-$\alpha$-phosphatidylethanolamine [PEA-(BOC)]

The title compound was prepared by heating a mixture of $\beta,\gamma$-dipalmitoyl-D,L-$\alpha$-phospatidylethanolamine (PEA, 1.40 g, 2.02 mmole), 2-(tert-butoxycarbonyloxyimino)-2-phenylacetonitrile (BOC-ON®, 0.60, 2.42 mmole), triethylamine (0.44 ml, 3.03 mmole) in 5 ml of 5% aqueous dioxane at 55° C. for 3 hrs. The resulting yellow solution was cooled, concentrated at reduced pressure to dryness. The crude product was purified on preparative TLC plates (EM silica gel 60 F$_{254}$, 2 mm) at the loading capacity of 0.25 g/plate. The chromatogram was developed with chloroform/methanol/H$_2$O (73:20:2). A faintly UV-adsorbing major band (Rf~0.6), which can be checked by cutting a narrow strip form the plate and visualized with ninhydrin spray at 100° C., was scraped and eluted with 300 ml of chloroform/methanol/H$_2$O (73:20:2). The eluent was concentrated to dryness. The residue was dissolved in 50 ml of CHCl$_3$, filtered and concentrated to dryness (1.56 g, 97%). The IR indicated carbamate absorption at 1710 cm$^{-1}$. NMR was consistent with the structure.

EXAMPLE 2

Preparation of
N-tert-Butyloxycarbonyl-$\beta$-$\gamma$-dipalmitoyl-D,L-$\alpha$-phosphatidylethanolamine, 2-(4-bromophenyl)-2-oxoethyl ester [PEA±(phenacyl) (BOC)]

A solution of PEA (BOC) (1.56 g, 1.97 mmole) and $\alpha$,p-dibromoacetophenone (0.82 g, 2.96 mmole) in 45 ml of DMF/THF (7:2) was treated with triethylamine (0.28 ml, 1.97 mmole) and stirred overnight at room temperature. The reaction mixture was concentrated at reduced pressure and the residue triturated with ethyl ether (100 ml) and filtered to remove insoluble solid. The filtrate and washings were confined and concentrated. The residue was dissolved in 15 ml of chloroform and applied to 8 preparative TLC plates and developed with 2% methanol/chloroform. A UV-absorbing, ninhydrin responsive band (Rf=0.2) was removed and eluted with 300 ml of 10% methanol/chloroform. Evaporation of the eluent gave a viscous oil (1.17 g, 60%). IR and NMR were consistent with the structure.

EXAMPLE 3

Preparation of
$\beta,\gamma$-Dipalmitoyl-D,L-$\alpha$-phospatidylethanolamine, 2-(4-bromophenyl)-2-oxoethyl ester [PEA±(phenacyl)]

A solution of PEA±(phenacyl) (BOC) (1.17 g, 1.18 mmole) in 8.4 ml of methylene chloride was treated with 3.6 ml of trifluoroacetic acid at room temperature for 30 min. The reaction was concentrated at reduced pressure. The residue was coevaporated with chloroform to remove the remaining acid. The product was purified on silica gel column (25 g. EM Silica Gel 60, 70–230 mesh) packed and eluted with chloroform and methanol/chloroform (2–7.5%) to remove all the side products and the desired product (0.96 g, 92%). IR and NMR were consistent with the structure. Fast Atom Bombardment (FAB) Mass Spectral analysis indicated molecular ions and m/e 388 and 890 corresponding to the isotopic bromine derivatives of the target compound.

EXAMPLE 4

Preparation of
N-Triphenylmethyl-$\beta$-$\gamma$-dipalmitoyl-D,L-$\alpha$-phosphatidylethanolamine [PEA-(Tr)]

A mixture of chlorotriphenylmethane (1.24 g, 4.48 mmole), triethylamine (0.58 g, 5.74 mmole) and $\beta$-$\gamma$-dipalmitoyl-D,L-$\alpha$-phosphatidylethanolamine in 40 ml CHCl$_3$ was heated at 55° C. for 6 hrs. The cooled reaction solution was extracted with H$_2$O and NaHCO$_3$ solution (0.1N), dried over Na$_2$SO$_4$, filtered and concentrated to an oil. Purification by silica gel (EM Silica Gel 60H) short column chromatography using CHCl$_3$/MeOH 0.5%–5% afforded the target compound (0.43 g, 46.5%).

EXAMPLE 5

Preparation of
N-Triphenyl-β-γ-dipalmitoyl-D,L-α-phosphatidyl ethanolamine, 2-(4-nitrophenyl)ethyl ester [PEA±(NPE) (Tr)]

PEA (Tr) (2.5 g, 2.68 mmole) was azeotroped three times with 10 ml dry pyridine dissolved in 17.8 ml dry pyridine and treated with 3-nitro-1,2,4-triazole (0.92 g, 8.04 mmole), 4-quinolinesulfonylchloride (0.92 g, 4.02 mmole) and 2-(4-nitrophenyl)ethanol (1.8 g, 10.72 mmole) for three days at room temperature. Additional 3-nitro-1,2,4-triazole (0.15 g, 1.32 mmole) and 4-quinolinesulfonylchloride (0.15 g, 0.65 mmole) were added and the reaction continued for one day. The reaction was terminated by addition of water and then azeotroped with toluene to remove pyridine. The product was purified using silica gel preparative TLC plates developed with 5% methanol/chloroform. Elution with 15% methanol/chloroform afforded the target compound (1.8 g, 62%). Elemental analysis, IR and FAB mass spectra were consistent with the assigned structure.

EXAMPLE 6

Preparation of
N-Triphenylmethyl-β-γ-dipalmitoyl-D,L-α-phosphatidylethanolamine, 2-(4-bromophenyl)-2-oxoethyl ester [PEA±(phenacyl) (Tr)]

A solution of PEA (Tr) (0.30 g, 0.317 mmole), α,p-dibromoacetophenone (0.13 g, 0.476 mmole), and triethylamine (0.046 ml, 0.317 mmole) in 20 ml of DMF/THF (1:1) was allowed to stand at room temperature for 20 hrs. and evaporated in vacuo. The residue was triturated with 50 ml of ether and filtered. The filtrate was evaporated and purified on preparative TLC plates developed with 1% methanol/chloroform. The major UV-absorbing band (Rf=0.2) was stripped and eluted with 5% methanol/chloroform. Evaporation of the eluent gave the desired compound (0.16 g, 44%). IR and NMR were consistent with the structure.

EXAMPLE 7

Preparation of
β-γ-Dipalmitoyl-D,L-α-phosphatidylethanolamine, 2-(4-nitrophenyl)ethyl ester [PEA±(NPE)]

PEA±(NPE) (Tr) (0.34 g, 0.317 mmole) was dissolved in 25.3 ml HOAC (glacial). 4.2 ml H$_2$O was added and the detritylation run for 16 hours at room temperature. The reaction mixture was concentrated, azeotroped with hexane, and extracted with chloroform and 0.1N NaHCO$_3$. The organic phase was dried over Na$_2$SO$_4$, concentrated and separated by silica gel short column chromatography using 1-5% methanol/chloroform. Elemental analysis, IR and FAB mass spectra were consistent with the assigned structure.

EXAMPLE 8

Preparation of
N-[2-[4-[2-(4-bromophenyl)-2-oxoethyloxycarbonyl]-5,5'-dimethyl-1,3-thiazolidinyl]-2-phenylacetamidoacetyl]-β,γ-dipalmitoyl-D,L-α-phosphatidylethanolamine, 2-(4-bromophenyl)-2-oxoethyl ester [PEA±(phenacyl)-(b)-PG(phenacyl)]

A solution of PEA±(phenacyl) (38 mg, 0.038 mmole), PG(phenacyl) (31 mg, 0.058 mmole) in 2 ml of chloroform was allowed to stand at room temperature for 20 hrs. and concentrated in vacuo. The crude product was purified on a silica gel column (3 g) packed and eluted with chloroform and chloroform/methanol (49:1 to 9:1) to give unreacted PG(phenacyl) (14 mg, 0.026 mmole) and the desired product (26 mg, 48%) IR and NMR were consistent with the assigned structure.

The preparation of 2-(4-bromophenyl)-2-oxoethyl benzylpenicillanate [PG(phenacyl)] is carried out as follows:

A mixture of potassium benzylpenicillanate (3.0 g, 8.06 mmole) and α,p-dibromoacetophenone (2.5 g, 9.16 mmole), in 60 ml of DMF/THF (1:1) at 5° C. was treated with triethylamine (0.82 g, 8.1 mmole) and stirred for 4 hrs. The reaction mixture was concentrated in vacuo and the residue was triturated with 50 ml of chloroform/ethyl ether (4:1) and filtered. The filtrate was concentrated to ~5 ml and purified by silica gel column chromatography using chloroform/ethylacetate (4:1) to give two fractions: (a) mixture of unreacted α,p-dibromoacetophenone and the desired product; and (b) pure desired product (2.05 g, 47%). IR and NMR were consistent with the structure.

EXAMPLE 9

Preparation of
N-[2-[4-[2-(4-bromophenyl)-2-oxoethyloxycarbonyl]-5,5'-dimethyl-1,3-thiazolidinyl]-2-phenylacetamidoacetyl]-β,γ-dipalmitoyl-D,L-α-phosphatidylethanolamine, 2-(4-nitrophenyl)-ethyl ester [PEA±(NPE)-(b)PG(phenacyl)]

The title compound was prepared by dissolving PEA±(NPE) (0.068 g, 0.08 mmole) and PG(phenacyl) (0.0699 g, 10.13 mmole) in 2 ml of CHCl$_3$. The solution was allowed to stand at room temperature for 20 hrs. and then concentrated to dryness. The residue was purified on silica gel column (5 g) packed & eluted with chloroform/ethyl acetate to recover unreacted excess PG(phenacyl) (0.033 g, 0.06 mmole) and the desired product (105 mg, 95%). IR & NMR were consistent with the structure. FAB Mass Spectral Analysis gave the molecular ion peak at m/e 1373 consistent with the structure.

EXAMPLE 10

Preparation of
N-[2-[4-carboxyl-5,5'-dimethyl-1,3-thiazolidinyl]-2-phenylacetamidoacetyl]-β,γ-dipalmitoyl-D,L-α-phosphatidylethanolamine [PEA-(b)PG]

Method A: A solution of PEA±(phenacyl)-(b)PG(phenacyl) (13 mg, 0.009 mmole), 1,8-diazabicyclo[5.4.0]undec-7-ene (10 mg, 0.06 mmole) in 0.5 ml of chloroform was allowed to stand at room temperature for 20 hrs. TLC analysis (EM silica gel 60 F 254, 0.25 mm) of the reaction mixture showed loss of PEA±(phenacyl)-(b)PG(phenacyl) and the generation of one product identical with that obtained in method B (Rf=0.27 in chloroform/methanol/H$_2$O=65:25:4).

Method B: A solution of PEA±(NPE)-(b)PG(phenacyl) (0.25 g, 0.18 mmole), 1,8-diazabicyclo[5.4.0]undec-7-ene (0.15 g, 0.98 mmole) in 2 ml of chloroform was allowed to stand at room temperature for 20 hrs. and then concentrated to a viscous oil. The residue was purified on preparative TLC plate developed with chloroform/methanol/H$_2$O (65:25:4). A UV-absorbing band (Rf=0.2) which is also responsive to iodoazide (Ref. 1) and molybdenum (Ref. 2) spray reagents was removed from the plate and eluted with the solvent. The eluent was concentrated to dryness. The residue was redissolved in 20 ml chloroform, filtered. The filtrate was reconcentrated to give the desired product (145 mg. 78%). FAB mass spectral analysis showed molecular ions for the mono, di- and tri-sodium salts of the target compound at m/e 1049, 1071 and 1093.

Reference 1:
D. Waldi in "Thin-Layer Chromatography," Ed. E. Stahl, p. 493.

Reference 2:
E. K. Ryu and M. MacCoss, J. Lipid Res. 20, 561 (1979)

EXAMPLE 11

Preparation of N-Succinyl-$\beta,\gamma$-dipalmitoyl-D,L-$\alpha$-phosphatidylethanolamine 2-(4-bromophenyl)-2-oxoethyl ester [PEA±(phenacyl)-Suc]

A solution of PEA±(phen) (70 mg, 0.078 mmole) in 2 ml of dimethylformide/chloroform mixture (1:1) was treated with succinic anhydride (9.5 mg, 0.095 mmole) and heated at 55° C. for 3 hrs. and evaporated in vacuo. The crude product was purified on preparative TLC plates (10×20 cm), developed with 15% methanol/chloroform. A UV-absorbing band (Rf=0.36) was stripped and eluted with 15% methanol/chloroform. The eluent was evaporated and the residue treated with 20 ml of chloroform, filtered and the filtrate evaporated to dryness (34 mg, 44%). The IR indicated an amide absorption and the NMR was consistent with the structure.

EXAMPLE 12

Conjugation of L-Thyroxine and $\beta,\gamma$-dipalmitoyl-D,L-$\alpha$-phosphatidylethanolamine 2-(4-bromophenyl)-2-oxoethyl ester via a succinamide ligand [PEA±(phenacyl)-SUC-T$_4$]

A solution of PEA±(phenacyl)-Suc (140 mg, 0.14 mmole) in 2 ml of methylene chloride was treated with dicyclohexyl carbodiimide (29 mg, 0.14 mmole). After appearance of a dicyclohexylurea precipitate (10 minutes), the reaction mixture was treated with L-thyroxine (112 mg, 0.14 mmole) and dimethylformamide (4 ml). The reaction mixture was evaporated to dryness after 4 hours at room temperature. The residue was triturated with 50 ml of ethyl ether and filtered and the filtrate was purified on preparative TLC plates developed with 15% methanol/chloroform. The UV-absorbing band with Rf=0.2 was stripped and eluted with chloroform/methanol/water (73:20:2). The eluent was evaporated and the residue treated with 40 ml of chloroform, filtered and evaporated to dryness (64 mg, 26%). Fast Atom Bombardment mass spectral analysis indicated molecular ions of m/e 1747 and 1749 corresponding to the isotopic bromine derivatives of the title compound.

EXAMPLE 13

Isolation of Succinamide Conjugate of L-Thyroxine and $\beta,\gamma$-dipalmitoyl-D,L-$\alpha$-phosphatidylethanolamine [PEA-SUC-T$_4$]

A solution of PEA±(phenacyl)-Suc-T$_4$ (64 mg, 0.037 mmole), 1,8-diazabicyclo[5.4.0]undec-7-ene (50 mg, 0.329 mmole) in 1 ml of chloroform was allowed to stand at room temperature for 24 hours. The evaporated residue was purified on preparative TLC plates developed with chloroform/methanol/H$_2$O (54:40:5). The UV-absorbing, molybdenum spray-responsive band (R$_f$=0.4) was stripped, eluted with the same solvent system. The eluent was evaporated and the residue treated with 40 ml of chloroform. The filtrate was evaporated to dryness. FAB mass spectral analysis on the residue (30 mg, 52%) showed a molecular ion of m/e 1550.

EXAMPLE 14

Preparation of Penicillin Tagged Liposomes

The procedure followed is a modification of that reported by Szoka and Papahadjopoulos [PNAS 75, 4194 (1978)], lecithin (egg, 25 mg, 0.032 mmole), cholesterol (12.7 mg, 0.032 mmole) and PEA-PG (1.5 mg, 0.0015 mmole) as obtained in Example 10, were placed in a 100 ml round bottom flask and evaporated to a thin film at reduced pressure. Diethyl ester (3.0 ml) and calf alkaline phosphatase solution (EC 3.1.3.1) (1.0 ml, 5000 units), in phosphate buffered saline (PBS) (10 mM phosphate buffer, 0.15M NaCl, pH 7.35) was added and sonicated for 5 minutes at room temperature. Ether was removed by evaporation at reduced pressure to give a gel. This was resuspended in PBS, dialyzed against PBS overnight at 5° C. and washed 4 times with PBS by centrifugation. The antigen tagged, enzyme laden liposomes were resuspended in 3.0 ml PBS and used directly in the assay.

EXAMPLE 15

Preparation of Thyroxine Tagged Liposomes with a Single Succinamide Ligand

Lecithin (egg, 25 mg, 0.032 mmole), cholesterol (12.7 mg, 0.032 mmole), dicetylphosphate (1.6 mg, 0.0029 mmole) and PEA-Suc-T4 (1.5 mg, 0.009 mmole), as obtained in Example 13, were treated as described in Example 14 to form antigen tagged, enzyme laden liposomes.

EXAMPLE 16

Coupling of $\beta,\gamma$-dipalmitoyl-D,L-$\alpha$-phosphatidylethanolamine 2-(4-bromophenyl)-2-oxoethyl ester and PG (phenacyl)-ED-Suc[PEA±(phenacyl)-Suc-ED-(b)-PG(phenacyl)]

A solution of Suc-ED-PG(phenacyl) (35 mg, 0.05 mmole) in 2 ml of methylene chloride/dimethylformamide (6:1) was treated with dicyclohexylcarbodiimide (10 mg, 0.05 mmole) for 10 min. until the DCU precipitation was observed. PEA±(phenacyl) (44 mg. 0.05 mmole) was added and the reaction mixture was stirred at room temperature for 2 hours. The evaporated crude product was purified on preparative silica gel TLC using 10% methanol/chloroform. An I.R. spectrum of the isolated product (Rf 0.43, 29 mg, 37%) was consistent with the assigned structure. The product gave a positive iodoazide test for sulfur and a weak ninhydrin test for amines.

The preparation of N-Succinyl-N'-[2-[4-[2-(4-bromophenyl)-2-oxoethyl-oxycarbonyl]-5,5'-dimethyl-1,3-thiazolidinyl]-2-phenylacetamidoacetyl]-ethylenediamine [Suc-ED-PG(phenacyl)] was carried out as follows:

A solution of PG(phenacyl) (0.50 g, 0.925 mmole) in 50 ml of chloroform was treated with ethylenediamine (ED) (0.22 g, 3.7 mmole) at room temperature for 3 hours. The crude product was purified on preparative TLC plates, developed with chloroform/methanol/water (43:50:7). A UV-absorbing band (Rf=0.28) was stripped and eluted with the same solvent system to give a solid residue (282 mg, 51%). This intermediate product (0.20 g, 0.332 mmole) was dissolved in 10 ml of dimethylformamide and treated with succinic anhydride (36 mg, 0.366 mmole) at 60° for 1 hour. Purification was carried out on preparative silica gel TLC using chloroform/methanol/H₂O (65:25:4) for developing and eluting. An IR spectrum of the isolated product (Rf 0.77, 38 mg, 12%) was consistent with the assigned structure and the product gave a positive test with iodoazide spray reagent for sulfur.

EXAMPLE 17

Preparation of Hemisuccinamidoethylamine conjugate of β,γ-diapalmitoyl-D,L-α-phosphatidylethanolamine and penicillin G [PEA-Suc-ED-(b)PG]

A solution of PEA±(phenacyl)-Suc-ED-(b)-PG(phenacyl) (22 mg, 0.014 mmole) in 0.5 ml of 5% methanol/chloroform was treated with 1,8-diazabicyclo-[5.4.0]undec-7-ene (22 mg, 0.14 mmole) at room temperature for 20 hours. After evaporation the residue was purified on preparative silica gel TLC (4×20 cm) developed with chloroform/methanol/H₂O (65:25:4). The desired product was obtained in the usual manner. The compound gave a positive iodoazide test for sulfur an molybdenum test for phosphorous. [E. K. Ryu and M. MacCoss, J. Lipid Res., 20, 561 (1979)]

EXAMPLE 18

Preparation of Penicillin Tagged Liposomes Containing a Double Succinamide Ethylenediamine Ligand Lecithin (egg, 25 mg, 0.032 mmoles), cholesterol (12.7 mg, 0.032 mmole) and PEA-suc-ED-PG (1.5 mg, 0.013 mmoles), as obtained in Example 17, were treated as described in Example 14 to form antigen tagged, enzyme laden liposomes.

What is claimed is:

1. A method of forming an analyte-functionalized liposome for use in immunoassays comprising the steps of:

a. obtaining an intermediate having the structure

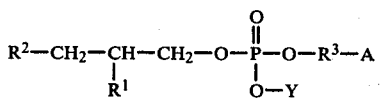

where $R^1$ and $R^2$ are independently selected from the group consisting of H, OH, R'', OR'' and

OCR'', (where R'' is selected from the group consisting of saturated, unsaturated, branched and straight-chain alkyl and alkylene groups of 1 to 24 carbons), wherein at least one of $R^1$ and $R^2$ is selected from the group consisting of

OCR'' and OR''; and where $R^3$ is a side chain with a functional group capable of bonding to the analyte desired to be attached, A is an analyte, and Y is a triester-blocking group;

b. reacting said intermediate to form an amphiphilic compound having the structure

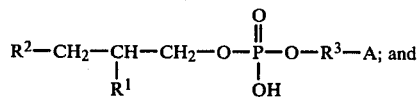

c. forming a liposome from the product of step (b) which is functionalized on its surface with said analyte and has a marker carried within said liposome.

2. A method of forming a ligand-functionalized liposome for subsequent attachment of an analyte to the ligand functional group to provide a compound for use in immunoassays wherein said ligand-functionalized liposome is derived from an intermediate having the structure

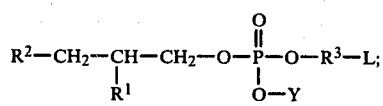

where $R^1$ and $R^2$ are independently selected from the group consisting of H, OH, R'', OR'' and

OCR''
O (where R'' is selected from the group consisting of saturated, unsaturated, branched and straight-chain alkyl and alkylene groups of 1 to 24 carbons), and wherein at least one of $R^1$ and $R^2$ is selected from the group consisting of

OCR''
O and OR''; and where $R^3$ is a side chain with a functional group capable of bonding to the ligand desired to be attached, Y is a triester-blocking group, and L is a ligand.

3. The method of claim 2, further comprising the steps of:

a. reacting said intermediate to form a compound having the structure

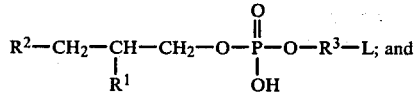

b. forming a liposome from the product of step (a) which is functionalized on its surface with said ligand and which has a marker carrier within said liposome.

4. The method of claim 3, further comprising reacting the product thus obtained to attach an analyte to the ligand functional group of the liposome.

5. The method of claim 2, further comprising the steps of:

a. reacting said intermediate to form a compound having the structure

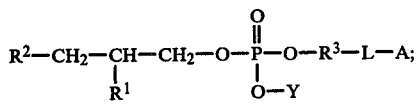

where A is an analyte;

b. reacting the product of step (a) to form a compound having the structure

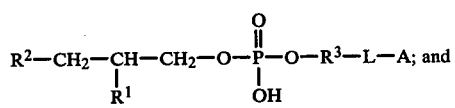

c. forming a liposome from the product of step (b) which is functionalized on its surface with said ligand attached to said analyte and which has a marker carried within said liposome.

6. A method of forming an analyte-functionalized liposome for use in immunoassays comprising the steps of:

a. reacting an analyte with a ligand to form a compound of the formula

L—A, where L is a ligand and A is an analyte;

b. reacting the compound of step (a) with a phospholipid compound of the formula

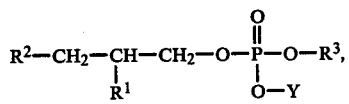

where $R^1$ and $R^2$ are independently selected from the group consisting of H, OH, R″, OR″ and

(where R″ is selected from the group consisting of saturated, unsaturated, branched and straight-chain alkyl and alkylene groups of 1 to 24 carbons), and wherein at least one of $R^1$ and $R^2$ is selected from the group consisting of

and OR″; and where $R^3$ is a side chain with a functional group capable of bonding to the ligand desired to be attached, and Y is a triester-blocking group; to form an intermediate having the formula

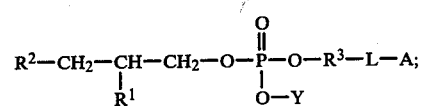

c. reacting said intermediate to form a compound having the structure

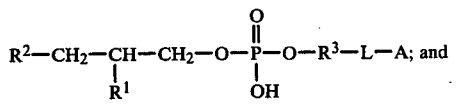

d. forming a liposome from the product of step (c) which is functionalized on its surface with said ligand attached to said analyte and which has a marker carried within said liposome.

7. The method of claim 1, claim 2 or claim 6, wherein said analyte is selected from a group of compounds and their derivatives which are capable of being coupled to the surface of liposomes, said group consisting of antigens, antibodies, circulating hormones, intracellular messengers, cyclic nucleotides, prostaglandins, therapeutic drugs, antibiotics, opiate drugs, ergot alkaloids, mycotoxins, natural toxicants, environmental food contaminants, and macromolecular antigens.

8. The method of claim 1, claim 2 or claim 6, wherein $R^1$ and $R^2$ are each of the formula

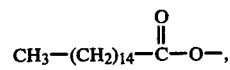

and wherein $R^3$ is of the formula

—CH$_2$—CH$_2$—NH—

9. A ligand-functionalized liposome prepared by the method of claim 2 or claim 3.

10. A ligand-functionalized liposome having an analyte attached to said ligand, prepared by the method of claim 4, claim 5 or claim 6.

11. In a method of forming an analyte-functionalized liposome for use in immunoassays wherein said liposome formed is functionalized on its surface with an analyte and has a marker carrier within said liposome, the improvement comprising the steps of:

a. obtaining an intermediate having the structure

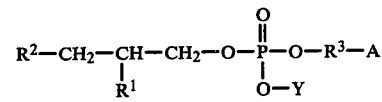

where $R^1$ and $R^2$ are independently selected from the group consisting of H, OH, R″, OR″ and

(where R″ is selected from the group consisting of saturated and unsaturated, branched straight-chain alkyl and alkylene groups of 1 to 24 carbons), wherein at least one of $R^1$ and $R^2$ is selected from the group consisting of

and OR″; and where $R^3$ is a side chain with a functional group capable of bonding to the analyte desired to be attached, A is an analyte, and Y is a triester-blocking group; and b. reacting said intermediate to form an amphiphilic compound having the structure

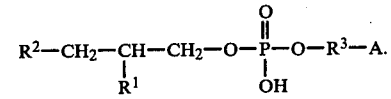

* * * * *